United States Patent [19]

Laughlin

[11] 4,067,961
[45] Jan. 10, 1978

[54] CONTROLLED RELEASE ARTICLE

[75] Inventor: Robert Gene Laughlin, Cincinnati, Ohio

[73] Assignee: The Procter & Gamble Company, Cincinnati, Ohio

[21] Appl. No.: 714,540

[22] Filed: Aug. 16, 1976

Related U.S. Application Data

[63] Continuation of Ser. No. 560,020, March 19, 1975, abandoned.

[51] Int. Cl.$^2$ .................... A61K 9/02; A61L 15/03
[52] U.S. Cl. .................... 424/15; 128/260; 424/14; 424/16; 424/21; 424/28
[58] Field of Search .................... 128/260; 424/14–27, 424/28; 210/500

[56] References Cited

U.S. PATENT DOCUMENTS

| | | | |
|---|---|---|---|
| 2,773,027 | 12/1956 | Powers | 210/500 X |
| 3,303,254 | 2/1967 | Simons | 210/500 X |
| 3,441,142 | 4/1969 | Oja | 210/500 X |
| 3,721,623 | 3/1973 | Stana | 210/500 X |
| 3,780,147 | 12/1973 | Stana | 210/500 X |
| 3,845,770 | 11/1974 | Thebunes et al. | 128/260 |
| 3,855,133 | 12/1974 | Roehsler | 210/500 X |
| 3,928,294 | 12/1975 | Crawford et al. | 210/500 X |
| 3,929,741 | 12/1975 | Laskey | 210/500 X |
| 3,945,926 | 3/1976 | Kesting | 210/500 X |
| 3,948,254 | 4/1976 | Zaffaroni | 128/127 |
| 3,961,628 | 6/1976 | Arnold | 128/260 |
| 4,031,202 | 6/1977 | Laughlin et al. | 424/28 |

FOREIGN PATENT DOCUMENTS 1,333,576  10/1973  United Kingdom.

OTHER PUBLICATIONS

C.A. 79#9901h, (1973).
C.A. 78#33929y, (1973).
C.A. 78#33917t, (1973).
C.A. 78#75866f, (1973).
Schwartz et al., Surface Active Agents, 1949 Interscience Pub., N. Y., pp. 313–315, "Micellle Structure".
Kirk–Othmer Encyclopedia of Chemical Technology, 2nd Ed., vol. 19, Surfactants, pp. 573–575, "Micelles".
Ralston Fattyacids and Their Derivatives, John Wiley & Sons, N.Y., pp. 660–707, "Micelles".
Solomons Organic Chemistry, John Wiley & Sons, N.Y., (1976), pp. 884–893, "Soap Micelles".
Hart et al., Organic Chemistry, 3rd Ed., Houghton–Mifflin, N.Y., pp. 214–217, "Soap Micelles".

*Primary Examiner*—Shep K. Rose
*Attorney, Agent, or Firm*—Jerry J. Yetter; Julius P. Filcik; Richard C. Witte

[57] ABSTRACT

Controlled release articles which regulate the concentration of a surfactant compound at a useful level in an environment external to said articles are provided. The articles are especially adapted for use in or on the bodies of animals, including humans, to provide controlled release of surfactants having biological activity, for example, non-hormonal contraceptives.

8 Claims, No Drawings

CONTROLLED RELEASE ARTICLE

This is a continuation, of application Ser. No. 560,020, filed Mar. 19, 1975, now abandoned.

BACKGROUND OF THE INVENTION

The present invention encompasses articles designed to provide controlled release of surfactant compounds. More specifically, the articles herein comprise a microporous membrane releasably enclosing a solution of a micelle-forming surfactant compound.

The desirability of providing metered dosage forms of biologically active or medicinal agents has long been recognized. Metered dosages can be manifest either as controlled release or sustained release of a given material. The distinction between "controlled release" and "sustained or prolonged release" has been recognized; see Cowsar, in "Advances in Experimental Medicine and Biology", Vol. 49, "Controlled Release of Biologically Active Agents", Ed. Tanquary and Lacey, Plenum Press, New York 1974. However, the terms are frequently used interchangeably. For the present purposes, "sustained release" articles are defined as those which prolong the time period over which a material is released into an external environment. Sustained release can be accomplished by incorporating a kinetic barrier to release within the article, e.g., diffusion through a polymer matrix. Conversely, the term "controlled release" as used herein encompasses articles which release material to an external environment in response to "need". In the controlled release system there is no persistent kinetic barrier to release within the article; instead, initial release to achieve an effective concentration of the material is rapid, and an external parameter controls this release. For example, in the medical uses of the present articles the concentration of active compound in the body fluids bathing the product is the controlling parameter. The major distinction between the two types of systems is that articles based on the controlled release principle operate by a feedback mechanism regulating release, whereas articles employing the sustained release mechanism do not. One parameter of the total system is influential with respect to whether controlled or sustained release ensues, namely, the volume of the external fluid. When the ratio of this volume to the membrane area available for diffusion is too high, feedback control never develops, and sustained, rather than controlled release, ensues.

Controlled release articles of the present type respond rapidly to changes such as dilution effects in the environment external to the article, e.g., by body fluid changes, whereas sustained release articles do not. The net result is that articles based on the principle of controlled release are capable of rapidly establishing an effective level or concentration of a medicament or other agent in a selected environment, and then shutting off release so as to maintain the concentration at that level. In contrast, sustained release articles simply dispense an agent at a constant rate. Such articles, therefore, do not display the feedback regulation of release that a controlled release article displays.

It will be recognized that articles operating by the controlled release mechanism provide substantial advantages over sustained release articles for certain uses. For example, placement of a properly formulated controlled release medicament system in an animal's body cavity in contact with body fluids very quickly establishes an effective concentration of the medicament in the fluids. This concentration is automatically maintained in response to dilution or depletion as additional fluids are secreted, or the medicament is bound to tissue, absorbed, etc. Accordingly, for uses such as in contraceptives where it is desirable to provide an effective amount of the contraceptive agent almost immediately, a controlled release system rather than a sustained release system is preferred.

It has now been discovered that solutions of micelle-forming surfactant compounds can be releasably enclosed in a container comprising a microporous membrane. Articles prepared in this manner are stable and do not suffer osmotic rupture when placed in body cavities in contact with body fluids. Rather, the stable articles provide controlled release of the surfactant into the body fluids. Proper selection of surfactant provides a means for achieving various biological effects, e.g., antimicrobial activity, spermicidal activity, and the like. While it will be recognized that the articles herein can be used in any situation where controlled release of a surfactant into an external fluid medium is desired (as long as the previously noted volume to area ratio is appropriate), the preferred articles are especially adapted for use in body cavities such as the vagina.

It is an object of the present invention to provide stable articles which furnish controlled release of a micelle-forming surfactant.

It is another object herein to provide articles adapted for use in contact with living tissue (human or lower animal) which furnish controlled release of biologically active surfactants.

It is another object herein to provide articles suitable for use as contraceptives.

These and other objects are obtained herein as will be seen from the following disclosures.

PRIOR ART

The following United States patents relate to articles comprising drugs enclosed within permeable membranes: U.S. Pat. No. 3,828,777 MICROPOROUS OCULAR DEVICE, issued Aug. 13, 1974 to R. A. Ness; U.S. Pat. No. 3,618,604 OCULAR INSERT, issued Nov. 9, 1971 to R. A. Ness; U.S. Pat. No. 3,416,530 EYEBALL MEDICATION DISPENSING TABLET, issued Dec. 17, 1968 to R. A. Ness; U.s. Pat. No. 3,832,252 METHOD OF MAKING A DRUG-DELIVERY DEVICE, issued Aug. 27, 1974 to T. Higuchi and H. M Leeper (see also U.S. Pat. No. 3,598,122, issued 10/1971, other references cited in Higuchi, et al., as well as U.S. Pat. No. 3,867,519.)

In general, the foregoing references relate to sustained release articles, rather than controlled release articles of the present type. The Higuchi, et al., patent illustrates the use of internal barriers in the article to achieve sustained drug release in the manner noted hereinabove.

Attwood and Florence, J. Pharm. Pharmac., 1971, 23, Suppl. 242S, briefly describe the dialysis of chlorpromazine across Visking membranes and suggest that this phenomenon may have applications in sustained release technology. Attwood, et al., do not suggest the use of surfactants of the present type in controlled release articles.

Lichtman, et al., Contraception 8(4) 291–7 (1973) describe a vaginal contraceptive device comprising a soluble film containing a nonionic surfactant as a spermicide.

U.S. Pat. No. 3,694,364 LAUNDERING AID, issued Sept. 26, 1972 to J. B. Edwards relates to surface-modified cellulose bags (e.g., terry cloth) containing detergents and their use in laundry baths.

SUMMARY OF THE INVENTION

In its broadest aspect, the present invention encompasses controlled release articles especially adapted to maintaining a useful concentration of a surfactant compound in an environment external to said articles. The articles herein comprise a solution consisting essentially of a micelle-forming surfactant compound and solvent, normally water, said solution having a concentration above the critical micelle concentration of the surfactant compound. The solution of the surfactant compound is releasably enclosed in an insoluble container (i.e., a container which maintains its physical integrity when in contact with fluids, especially water or biological fluids such as serum) at least part of the wall of said container comprising a microporous membrane. Surfactants employed in the preferred articles herein designed for use in the body cavities of animals are characterized by an "R" value (as defined more fully hereinafter) greater than about 1.

More specifically, preferred articles herein are designed for use as between-menstrual period contraceptives. Such articles comprise an envelope made wholly or partly of a microporous polymeric diffusion membrane (preferably cellulose) enclosing a solution of spermicidal surfactant at a concentration greater than the critical micelle concentration (cmc) of the surfactant. The term "spermicidal" as employed herein is intended to encompass surfactants which truly "kill" animal sperm, as well as those which immobilize or otherwise render sperm cells inactive.

The controlled release articles herein function by means of diffusion of surfactant monomer through the solvent medium (typically water or biological fluids such as serum) in the pores of the microporous portion of the enclosing envelope. The micellar solution of surfactant remaining in the envelope serves as a reservoir which automatically releases additional surfactant monomer when the external monomer concentration is decreased.

Articles of the present type employing surfactant solutions as the active ingredient have several important advantages over other types of metered dosage systems, and these advantages are perhaps best appreciated when considering the use of the articles as contraceptives.

The use of micelle-forming surfactants as the active ingredient in the articles also maintains the osmotic pressure therein at a relatively low level. Accordingly, the pressure differential across the enclosing container is relatively small, and the container is stable and does not rupture. This desirable attribute of the present articles is to be contrasted with the situation which occurs when a similarly concentrated solution of a non-micelle-forming solute of similar molecular weight is enclosed in a diffusion membrane, whereupon osmotic pressures of tens or hundreds of atmospheres can be developed, thereby leading to rupture of the membrane.

Moreover, the surfactants employed as the active ingredients of the contraceptive articles of the present invention appear to function by an entirely localized effect on motile sperm. Accordingly, undesirable side-effects which can accompany the use of systemic contraceptive drugs such as hormones are avoided.

In addition, the use of safe, effective surfactants as the spermicide permits the formulator of the articles to employ a large excess of the spermicide therein. Controlled release allows formulation of articles containing more spermicide than the usual expected need but (1) reduces the probability of side-effects by regulating the concentration to a maximum level, and (2) allows for unusual variations in the amount of compound required or in the time period over which it might be needed. Accordingly, a "safety factor" of the order of 1000-fold vis-a-vis contraceptive efficacy can be provided by the articles.

Finally, the contraceptive articles herein are designed for use in the vagina. Accordingly, the articles can be inserted by the user and do not require fitting by a physician as, for example, in the case of intrauterine devices. The articles can be retained in the vagina during the time between menstrual periods to provide the desired prolonged contraceptive protection.

DETAILED DESCRIPTION OF THE INVENTION

The present articles are comprised of multiple components, each of which are described in detail hereinafter.

SURFACTANT

The surfactants employed in the instant articles and processes are characterized by several parameters which can vary somewhat, depending on the ultimate use of the articles. In general, the surfactants are selected from those which, in combination with a microporous membrane (as described more fully hereinafter), provide an appropriate relationship between release and the desired end use of the article, e.g., spermicidal activity.

The surfactants herein are characterized by their ability to dissolve in a solvent (normally water) and to form an association colloid therein. The grossly anomalous (low) osmotic pressures displayed by concentrated solutions of the surfactants herein are attributable to the association of surfactant monomers into micellar structures. This phenomenon is of considerable practical significance in that it allows fabrication of articles containing surfactants at extraordinarily high concentrations, as compared with concentrations permitted with other, non-associative types of solutes, without osmotic rupture of the enclosing membrane. In order to realize fully the unique advantages of surfactants in this regard, it is preferred to use those surfactants having a cmc of at most about $1 \times 10^{-3}$ molar (M).

When intended for use as between-period contraceptives or to provide other desirable effects such as the controlled release of antimicrobial surfactants, it is, of course, necessary to select surfactants which produce the desired biological response. Moreover, to secure the benefits of controlled release it is necessary also to select surfactants whose monomers are rapidly transported through the diffusion membrane to establish an effective concentration of surfactant in the medium external to the article.

From the foregoing consideration it will be appreciated that the desired biological response of a surfactant can be tested in vitro in a medium (such as physiological saline, which closely approximates various boly fluids) to determine the concentration at which the surfactant must be present in such medium to provide the desired response. Surfactants whose monomers are transported through the enclosing membrane of the article to provide at least the aforesaid effective concentration in the saline are useful herein. Over a given time period, the controlled release articles herein produce a stable maximum (or "plateau") concentration of surfactant in the external fluids. The magnitude of this plateau concentration is related to the cmc of the surfactant compound, and is approximately equal to the cmc. It follows that, for the desired effect to be realized, the ratio, R, of the cmc of the surfactant to its biologically effective concentration, $C_{biol.}$, in saline, i.e., $$R = cmc/C_{biol.}$$

must be greater than about 1. Similar considerations hold for external media other than saline, i.e., fluid media such as body fluids, water, etc., in which the present surfactant monomers are soluble. Accordingly, the preferred compounds for use in the articles described herein have values of R which are > ca. 1, i.e., $$R > ca. 1.$$

It will be recognized that a variety of surfactants exhibit a cmc less than the requisite about $10^{-3}M$ and meet this criteria for use in the present controlled release articles. Moreover, several surfactant types having the requisite cmc provide desirable biological responses, e.g., microbiocidal or static activity and/or spermicidal activity. Moreover, several surfactants exhibit the requisite relationship, $R >$ ca. 1, between cmc and biological activity.

Based solely on the foregoing considerations, representative examples of surfactants useful herein include nonionic surfactants such as $C_{10}H_{21}(OCH_2CH_2)_5OH$ (abb. $C_{10}EO_5$) and $C_{10}H_{21}(OCH_2CH_2)_6OH$ ($C_{10}EO_6$); semipolar surfactants such as $C_{12}H_{25}S(NH)_2CH_3$ and $C_{12}H_{25}(CH_3)_2AsO$; and cationic surfactants such as $C_{16}H_{33}N^+(CH_3)_3,Cl^-$ and $C_{16}H_{33}N^+C_5H_5,Cl^-$. These surfactants are characterized by $R \geqq 2$ and cmc $< 10^{-3}M$.

It is to be understood that other surfactants having the requisite cmc of $10^{-3}M$, or less, but which exhibit lower biological activity (especially as spermicidal agents), i.e., surfactants wherein ca. $1 < R < 2$, can be employed in the instant articles. However, the biological response to these latter surfactants is somewhat less than that of the preferred group, and the efficacy margin, i.e., R-1, is not as great. Included among this group of surfactants are $C_{12}EO_9$; $C_{16}EO_1SO_4^-,Na^+$; $C_{12}(CH_3)_2PO$; $C_{10}EO_4$; $C_{12}(C_2H_5)PO$; $C_{16}$ ammoniopropanesulfonate; $\beta$-$OHC_{12}(CH_3)_2PO$; and nonylphenol nonaethoxylate.

As can be seen from the foregoing, various surfactant types are useful in the controlled release articles herein. However, when articles designed for use as between-period contraceptives are being prepared, additional physio-chemical properties of the surfactants must be considered. For example, the surfactants should be toxicologically acceptable for use in the body over extended time periods. The surfactants should also be non-irritating to the delicate tissues of the vagina and uterus. The surfactants should not substantially bind serum proteins found in the vaginal area between periods of menstrual flow, inasmuch as the bound surfactant-protein moiety does not function as a spermicide and accelerates the depletion of surfactant from the reservoir within the article. Finally, the surfactant should be selected from those which do not bind to ionically charged sites in the enclosing diffusion membrane, since binding leads to unregulated transport through the membrane.

Based on the foregoing factors, and considering the high spermicidal activity of the compounds, the $C_{10}EO_5$ and $C_{10}EO_6$ surfactants are most preferred for use in the present contraceptive articles. As between these latter compounds, $C_{10}EO_5$ has the advantage of the lower molecular weight, and therefore provides more monomer per given weight of compound. Accordingly, $C_{10}EO_5$ is most preferred for use in the between-period, controlled release contraceptive articles of this invention.

It will be recognized that the surfactants disclosed hereinabove are all well-known from the detergency arts and can be made by various art-disclosed processes.

It is to be understood that mixtures of surfactants result in the formation of mixed micelles and preferential migration of the more soluble monomer. Monomer release from mixed surfactants is, therefore, not rigorously controlled and, while such mixtures are operable, they are not preferred for use herein.

CONTAINER

Broadly, the present articles comprise the surfactant solution and a container therefor. At least one portion of the container comprises a microporous membrane which permits the controlled release of surfactant monomers into the environment external to the container, but which prevents the transport of the larger surfactant micelles. In short, the membrane acts as a selective "sieve" at the colloidal/molecular level.

Containers used in the present articles can be partly made of any stable material such as glass, plastic, etc., which is not permeable, even to surfactant monomers. At least some portion of such containers must comprise the microporous membrane to allow controlled monomer release. Preferred articles are those wherein the container comprises an envelope of the membrane.

Membranes useful herein are characterized by parameters which reflect the membrane's strength, integrity and ability to act as a selective "sieve" for surfactant monomers, as follows.

The membranes should be substantially water-insoluble so that they maintain their strength and integrity when in contact with body fluids. (Of course, if the articles are to be used in contact with other types of fluids, appropriate solubility relationships must be considered.)

The membranes should be of a thickness (wet) less than about 150 microns ($\mu$) and are most preferably about 25-50$\mu$ thick (wet). Membranes thicker than about 150$\mu$ (wet) tend to impede release of surfactant monomer, whereas thicknesses below ca. 5-10$\mu$ (wet) cause the articles to be subject to osmotic rupture even by the relatively low osmotic pressures of the concentrated surfactant solutions used in the articles.

When the articles are to be used in contact with body fluids and tissues, as in the contraceptive articles herein, the membranes should be toxicologically acceptable. Moreover, the membrane material will most preferably be immunoligically acceptable and will not be rejected by the body's natural defense mechanisms nor have any untoward effect on the rate of antibody formation, and the like.

Finally, the membrane must have the ability to act as a sieve for the surfactant monomers in order to provide the controlled release benefit of the article. An important consideration in this regard is that the surfactant must not be soluble to any substantial extent in the membrane material. If the surfactant were to be soluble in the membrane material, uncontrolled release would ensue.

The membranes employed herein comprise a solid wall material having multiple miniscule pores therethrough, i.e., are microporous. The pores of the membrane are filled, or substantially filled, with solvent (e.g., water) for the surfactant monomer. In use in the containers of the instant articles, surfactant monomers migrate from the inner reservoir of surfactant solution to the external environment by means of diffusion through the solvent in these solvent-filled pores, which pores extend from inner to outer surfaces of the articles.

It will be appreciated by those skilled in the art that pore diameters of the membranes herein cannot be specified in absolute terms. Indeed, when dealing with pore sizes at the molecular level (i.e., at the dimensions of surfactant monomers), measurement techniques are only indirect and generally constitute a determination of which molecules (or association colloids) will pass through a given membrane and which will be retained, coupled with approximations of the molecular dimensions of the molecules that do pass.

Based on the foregoing, the pores in the membranes used in the present articles are characterized by diameters on the order of the size of the surfactant monomers herein, but are smaller than the surfactant micelles (i.e., association colloids comprising ca. 100–1000 monomer units). An experimental Surfactant Transport Procedure for selecting microporous membranes having the appropriate pore size for use in the articles is set forth below.

Membranes suitable for use as the container can be made from any material which possesses the above-described characteristics and properties. For example, suitably perforated polyethylene, polypropylene, polyvinylchloride, etc., sheeting can be used in the present articles.

Highly preferred membranes herein are prepared from water-swellable polymers such as polyvinyl alcohol (suitably modified so as to be water-insoluble) and cellulose. Cellulose is a highly preferred membrane material, inasmuch as it has a long history of safety when used in prolonged contact with animal tissue. Such swellable polymers (or polymer precursors) can be cast into membranes which swell to about 1.8 to 2.0 times their dry thickness on contact with water. This swelling action automatically opens pores in the polymer membrane, and these pores are of the proper size to permit passage of surfactant monomers, and to prevent passage of surfactant micelles, through the membrane.

Methods for casting swellable cellulose membranes are well-known and form no part of this invention. In general terms, a cellulose derivative (e.g., cellulose acetate) is dissolved in a suitable solvent (e.g., acetone) and the solution is spread onto a smooth surface, whereupon the solvent evaporates leaving a continuous film of the cellulose derivative. The film of cellulose derivative is thereafter converted back to cellulose (e.g., with aqueous ammonia in the case of cellulose acetate) and swollen with water to provide a membrane suitable for use as the container of the present articles.

As will be appreciated from the foregoing, a variety of materials can be used as the membranous container portion of the controlled release articles, with solvent-swellable polymers being the most preferred due to their inherent sub-microscopic porosity in the swollen state. An experimental procedure which can be used to select membranes for use herein is as follows.

Surfactant Transport Procedure

A cell for testing transport of surfactant monomers through membranes is as follows. A 40 mm (diameter) × 50 mm (length) poly-methylmethacrylate rod is halved and each half is suitably machined to provide cavities 16 mm (diam.) × 10 mm (depth), such that the cavities abut when the rod halves are reassembled. Each cavity is provided with two inlet holes for filling and sampling. A brass clamp is used to hold the two cell halves firmly together.

The surfactant transport is carried out in the following manner. A 4 cm. × 4 cm. square of the membrane material to be tested is sandwiched between the cell halves, enclosing a 3 mm. glass head on each side of the membrane to provide stirring. The cell cavities are filled with saline and the inlet holes plugged with waterproof tape. After equilibrating overnight at 37° C, the saline in one half of the cell is replaced with a solution of known concentration of radiotagged surfactant. The inlet hole is again taped, and the cell is placed in a 37° C bath in a device which allows the cell to be rotated axially at 50 rpm. Periodically, the cell is raised from the bath and the solution in the desired compartment sampled.

A typical procedure using a membrane cut from viscose cellulose dialysis tubing (Matheson Scientific, 18970-20) is as follows. After equilibrating the cell and charging one side with surfactant as above, the cell is maintained in the 37° C bath for varying time periods, after each of which the tape is removed from the inlet holes and 10 microliter ($\mu$l) samples are removed by syringe. The samples are expressed below the surface of 100 $\mu$l of distilled water in a counting vial. In the subsequent scintillation counting, each sample vial is charged with 10 $\mu$l of a solution of 0.8% 2-diphenyloxazole and 0.01% of 1,4-bis-[2-(4-methyl-5-phenyloxazolyl)]-benzene in a 1:1 ethanol/toluene mixture. The vials (one for each time period) are then placed in the refrigerator compartment of a counting instrument and cooled to 4° C before being counted for 5 minutes each. The counts per minute are converted to ppm by applying a factor found by counting one or more standard samples. By taking samples at regular intervals, a curve plotting the surfactant concentration in the initially surfactant-free side of the cell versus the time of sampling can be drawn which describes the transport of the surfactant across the membrane.

Following the Surfactant Transport Procedure set forth hereinabove, the cell cavity designated (A) is charged with surfactant solution and the cavity designated (B) is charged with saline. The cell, whose cavities are separated by the test membrane, e.g., swollen, microporous cellulose dialysis tubing (dry thickness 25$\mu$; swollen thickness 50$\mu$) is then equilibrated in the indicated manner. The concentration of surfactant transported to cavity (B) is determined in the foregoing manner, and the graph of the concentration of surfactant in (B) v. time is plotted.

A plot of the concentration (B) as the ordinate and time ($t$) as the abscissa describes a monomer transport curve which rises sharply at the outset, and which gradually flattens. The slope of the sharply rising portion of the curve (i.e., over the first two hours of surfactant monomer transport) is the primary slope, $S_1$, and that of the flattened portion of the curve (i.e., 20 hours, and longer, of monomer transport) is the secondary slope, $S_2$.

For controlled release articles of the present type, the combination of surfactant and membrane should yield a monomer transport curve wherein $S_1$, i.e., $$(d[B]/dt); t = 0 - 5 \text{ hrs.}$$

is reasonably steep, and $S_2$, i.e., $$(d[B]/dt); t > 20 \text{ hrs.}$$

is reasonably flat, ideally zero. The intercept at zero time of the secondary transport data, having slope $S_2$, should be about equal to the cmc of the surfactant being tested. The ratio of $S_2/S_1$ is from 0 to about 0.1. $S_1$ should be no less than about $50 \times 10^{-6}$ moles $l^{-1}$ hr.$^{-1}$, and preferably should be in the range of about $200 \times 10^{-6}$ moles $l^{-1}$ hr.$^{-1}$ to about $750 \times 10^{-6}$ moles $l^{-1}$ hr.$^{-1}$.

Based on the foregoing, surfactant/membrane combinations can be selected which will provide controlled release articles of the present type. A highly preferred article herein which is particularly useful as a vaginal contraceptive comprises from about a 5% to about a 50% (wt.) aqueous solution of $C_{10}EO_5$ enclosed within a microporous, swollen cellulose membrane (dry thickness ca. $25\mu$; swollen thickness ca. $50\mu$).

The following non-limiting examples illustrate controlled release articles of the present type suitable for use as vaginal contraceptives, and the like.

EXAMPLE I

A flat sheet of commercial cellulose acetate about $75\mu$ thick and measuring about 7 in. × 10 in. is subjected to thermoforming methods known in the art to produce six hemispherical indentations 1 in. in diameter in the sheet. These indentations are filled to ca. 25% of their total volume with pure $C_{10}EO_5$ surfactant (using ca. 1 ml. of surfactant). A second flat sheet of cellulose acetate film is solvent-sealed over the original sheet covering the indentations using techniques known in the art.

The individual, filled and sealed indentations are then cut from the composite sheet to provide six articles which are then immersed in a 7.4 M ammonia solution containing 10% by weight sodium chloride for the 96 hours at 50° C. This ammonia treatment regenerates cellulose by deacetylating the cellulose acetate. Water passes through the membrane under the influence of osmotic forces during the deacetylation, partially filling the sealed articles.

Following the ammonia treatment, the articles are immersed in distilled water, whereupon they fill completely under the influence of osmosis, the entrapped air diffusing out leaving an article consisting of a closed container of regenerated cellulose enclosing a ca. 25% solution of $C_{10}EO_5$ surfactant.

An article of the foregoing type exhibits a monomer transport curve with $S_2/S_1$ of ca. 0.

An article of the foregoing type is placed in the vagina posterior to the introitus. The article is worn during the time between menses and safely delivers a spermidically effect amount of $C_{10}EO_5$ to the vaginal area.

In the article of Example I the $C_{10}EO_5$ is replaced by an equivalent amount of $C_{10}EO_6$ and equivalent results are secured.

In the article of Example I the pure $C_{10}EO_5$ is replaced by an equivalent amount of a 90:10 (wt.) mixture of $C_{10}EO_5$ and $C_{10}EO_6$ and good spermicidal activity over about a 21-day period is secured.

EXAMPLE II

An article especially adapted for providing controlled release of a surfactant compound into an external environment of relatively small volume and moisture content is as follows.

Polyethylene tubing ca. 2 mm. diameter × 5 cm. long is dipped in a solution of cellulose acetate/acetone and withdrawn, thereby depositing a film of cellulose acetate on the tubing. The acetone solvent is allowed to evaporate, thereby solidifying the cellulose acetate on the tubing. The cylindrical cellulose acetate film (thickness of about $25\mu$) is thereafter removed from the polyethylene form and one end is sealed by dipping in a droplet of cellulose acetate/acetone.

The foregoing cylinder, sealed at one end, is filled to about 75% of its volume with a 50% (wt.) aqueous solution of decyldimethylphosphine oxide surfactant. The open end of the cellulose acetate cylinder is sealed in the above-described manner.

The cylinder containing the phosphine oxide solution is deacetylated using 3.7 M aqueous ammonia containing 10% sodium chloride at room temperature for 48 hours. Thereafter, the filled cylinder is immersed in water for several hours, allowing most of the residual ammonia and sodium chloride to diffuse into the water bath.

An article prepared in the foregoing manner is especially useful as a glass de-fogging agent under conditions of high humidity. For example, an article of the above type is taped on the internal side of the face plate of a diving mask out of the field of view. When placed over the diver's face, the usual fogging of the face plate caused by the formation of small water droplets thereon is avoided by the release of the surfactant from the article.

What is claimed is:

1. A controlled release article especially adapted to maintaining a useful concentration of a spermicidal surfactant compound in the vagina, comprising:
   a. a solution consisting essentially of:
      i. a micelle-forming nonionic spermicidal surfactant compound, and
      ii. water, said solution having a concentration above the critical micelle concentration of the spermicidal surfactant compound, said solution being releasably enclosed in;
   b. a stable, insoluble container, at least part of the wall of said container comprising a microporous cellulose membrane.

2. An article according to claim 1 wherein the spermicidal surfactant compound is characterized by a critical micelle concentration of at most about $1 \times 10^{-3}$ Molar.

3. An article according to claim 2 wherein the combination of spermicidal surfactant solution and membrane exhibits a monomer transport curve having a ratio of slopes $S_2/S_1$ in the range of 0 to about 0.1.

4. An article according to claim 3 wherein the spermicidal surfactant has an R value greater than 1.

5. An article according to claim 1 wherein the spermicidal surfactant is a nonionic surfactant selected from ethylene oxide condensates of aliphatic alcohols.

6. An article according to claim 5 wherein the nonionic surfactant is $C_{10}EO_5$.

7. An article according to claim 5 wherein the nonionic surfactant is $C_{10}EO_6$.

8. An article according to claim 1 wherein the nonionic spermicidal surfactant is selected from $C_{10}EO_5$ or $C_{10}EO_6$, or mixtures thereof, and the microporous membrane is water-swollen cellulose having a dry thickness of ca. 5–25$\mu$ and a swollen thickness of ca. 10–50$\mu$.

* * * * *